US00PP27846P3

(12) United States Plant Patent
Bourne

(10) Patent No.: US PP27,846 P3
(45) Date of Patent: Apr. 4, 2017

(54) ***DIANTHUS* PLANT NAMED 'WP15 VAL11'**

(50) Latin Name: *Dianthus×allwoodii*
Varietal Denomination: WP15 VAL11

(71) Applicant: Plant Genetics International Ltd., Hampshire (GB)

(72) Inventor: Carolyn Grace Bourne, Devon (GB)

(73) Assignee: Plant Genetics International Ltd., Hampshire (GB)

( * ) Notice: Subject to any disclaimer, the term of this patent is extended or adjusted under 35 U.S.C. 154(b) by 0 days.

(21) Appl. No.: 14/757,323

(22) Filed: Dec. 16, 2015

(65) Prior Publication Data

US 2016/0183434 P1 Jun. 23, 2016

(30) Foreign Application Priority Data

Dec. 18, 2014 (QZ) ..... PBR 2014/3489

(51) Int. Cl.
*A01H 5/02* (2006.01)

(52) U.S. Cl.
USPC ..... Plt./276

(58) Field of Classification Search
USPC ..... Plt./276, 281
CPC ..... A01H 5/0233
See application file for complete search history.

*Primary Examiner* — Kent L Bell

(74) *Attorney, Agent, or Firm* — Bethany R. Roahrig; James M. Weatherly; Cochran Freund & Young, LLC

(57) ABSTRACT

A new cultivar of *Dianthus* plant named 'WP15 VAL 11' that is characterized by a compact mounding habit, double light pink flowers with a fuchsia eye, ruffled petals, blooming from May through October, with a strong, sweet fragrance, glaucous blue green foliage, suitable for use as a flowering plant in pots and containers as well as for use as a cut flower and in bouquets, is disclosed.

2 Drawing Sheets

Genus and species: *Dianthus×allwoodii.*
Variety denomination: 'WP15 VAL11'.

CROSS REFERENCE TO RELATED APPLICATIONS

This application claims the benefit of priority under 35 U.S.C. 119 (f) to the application for European Community Plant Variety Rights which was filed for the instant plant variety on Dec. 18, 2014, File Number 2014/3489.

BACKGROUND OF THE NEW PLANT

The present invention relates to a new and distinct cultivar of hardy *Dianthus*, commonly known as Garden Pink, which is grown for use as a flowering plant for pots and containers and for planting in the garden and landscape. The new cultivar is known botanically as *Dianthus×allwoodii* and will be referred to hereinafter by the cultivar name 'WP15 VAL11'.

'WP15 VAL11' is a complex hybrid plant that is the product of a long term breeding program conducted in a cultivated area of Houndspool, Dawlish, Devon, United Kingdom. 'WP15 VAL11' was selected in 2011 for its double delicate light pink flowers with a fuchsia eye, ruffled petal edges, strong, sweet fragrance and glaucous blue-green foliage.

'WP15 VAL11' arose and was selected as a seedling which resulted from the controlled pollination of two prior selections of *Dianthus*. The male parent is *Dianthus* code name 'MOW 02.09' (unpatented and unreleased) and the female parent is *Dianthus* code name 'VAL 05.15' (unpatented and unreleased). The male parent and female parent had both grown within the inventor's stock of breeding lines.

Asexual reproduction of 'WP15 VAL11' was first accomplished in 2011 in a cultivated area of Houndspool, United Kingdom using the propagation method of shoot cuttings. 'WP15 VAL11' has been determined to be stable and reproduces true to type in successive generations of asexual propagation.

SUMMARY

The following traits have been repeatedly observed and represent the characteristics of the new *Dianthus* cultivar 'WP15 VAL11'. 'WP15 VAL11' has not been tested under all possible conditions and phenotypic differences may be observed with variations in environmental, climatic and cultural conditions, however, without any variance in genotype.

1. 'WP15 VAL11' exhibits a compact mounding habit.
2. 'WP15 VAL11' bears double light pink flowers with a fuchsia eye.
3. The petals of 'WP15 VAL11' are ruffled.
4. 'WP15 VAL11' blooms from May through October.
5. The flowers of 'WP15 VAL11' exhibit a strong, sweet fragrance.
6. 'WP15 VAL11' exhibits glaucous blue green foliage.
7. At maturity, the height of the foliage mound of 'WP15 VAL11' is 40 cm, and the width is 30 cm to 35 cm.
8. 'WP15 VAL11' is perennial and is hardy at least to minus 15° Centigrade.
9. 'WP15 VAL11' is suitable for use as a flowering plant in pots and containers, and for use as a cut flower and in bouquets.

BRIEF DESCRIPTION OF THE PHOTOGRAPHS

The accompanying color photographs illustrate the overall appearance of the new *Dianthus* variety 'WP15 VAL11' showing colors as true as it is reasonably possible to obtain in colored reproductions of this type. Colors in the photographs may differ from the color values cited in the detailed botanical description, which accurately describe the actual colors of the new variety 'WP15 VAL11'.

Figure 1:
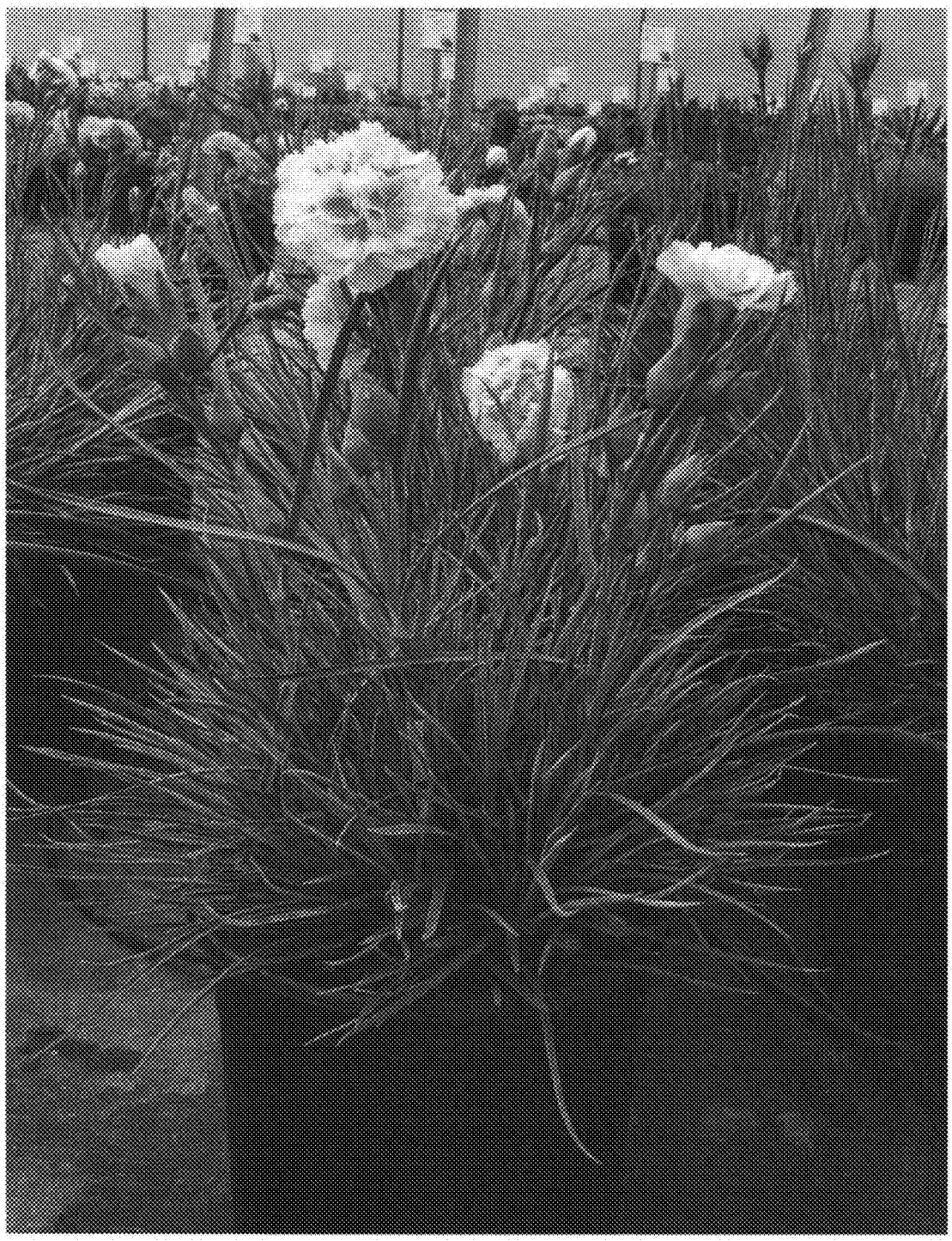
FIG. 1 depicts an entire flowering plant of 'WP15 VAL11'.
Figure 2:
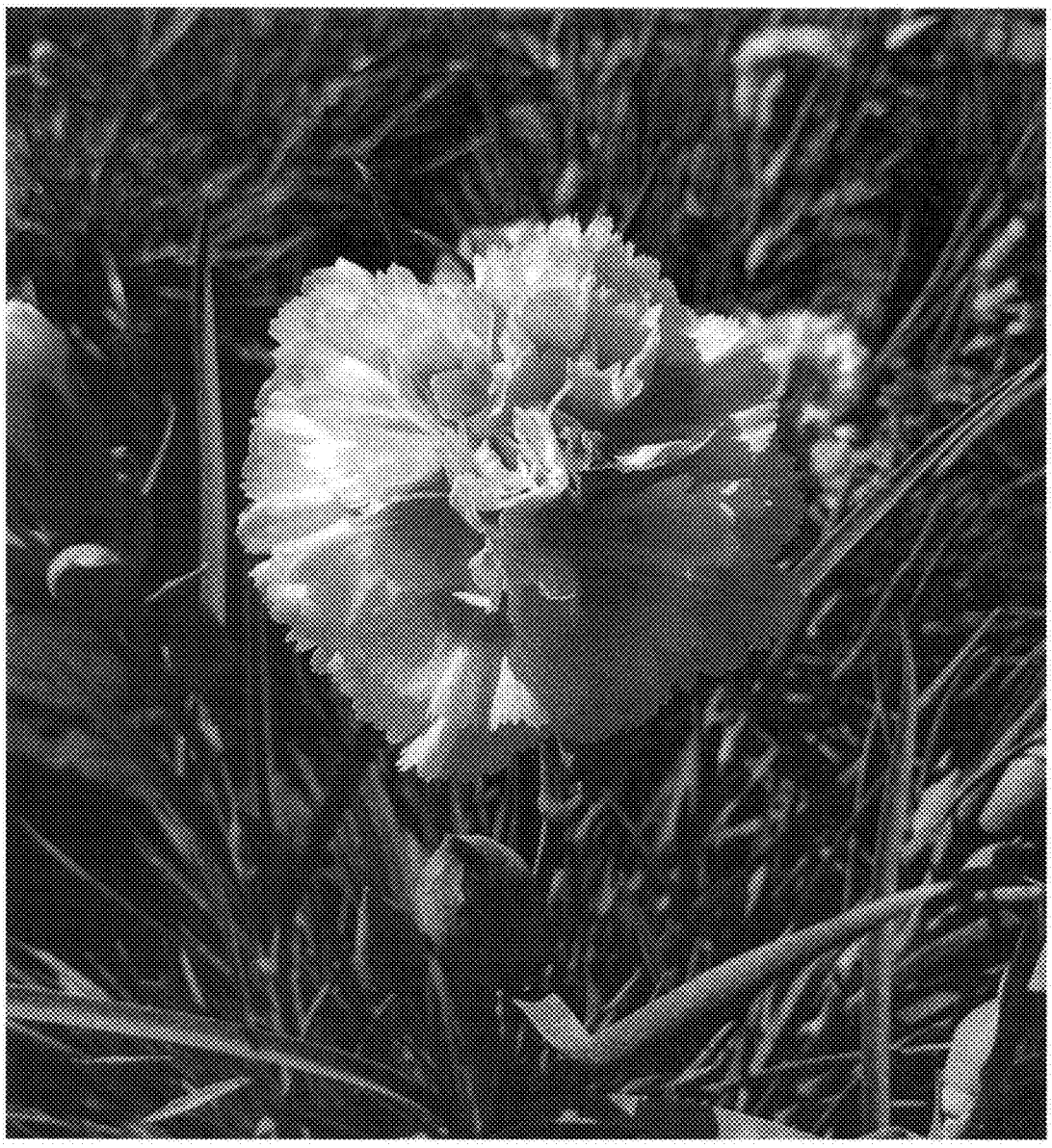
FIG. 2 depicts a close-up view of the flower of 'WP15 VAL11'.

Photographs were taken in August 2015 in Oxnard, Calif. of five-month old plants which have been grown outdoors in 1.5-liter containers. No chemicals were used to treat the plants. All photographs were made using conventional techniques and although colors may appear different from actual colors due to light reflectance they are as accurate as possible by conventional photography.

BOTANICAL DESCRIPTION OF THE PLANT

The following is a detailed description of the new cultivar 'WP15 VAL11'. Data was collected from plants grown in 3-liter containers under an unheated glasshouse in Houndspool, United Kingdom. The color determinations are in accordance with the 2001 edition of The Royal Horticultural Society Color Chart of The Royal Horticultural Society, London, England, except where general color terms of ordinary dictionary significance are used. No chemicals were used to treat the plants. Growing conditions are typical to other *Dianthus*.

Botanical classification: *Dianthus*.

*Variety*.—'WP15 VAL11'.

*Species*.—×*allwoodii*.

*Common names*.—Hybrid *dianthus*, Garden Pink.

*Commercial classification*.—Hardy perennial.

*Use*.—Ornamental plant for pots and containers.

Parentage: 'WP15 VAL11' is a hybrid plant that resulted from the controlled cross pollination between two *Dianthus*×*allwoodii* plants.

*Female parent plant*.—'VAL 05.15' experimental *Dianthus* plant (unpatented).

*Male parent plant*.—'MOW 02.09' experimental *Dianthus* plant (unpatented).

Plant description:

*Bloom period*.—May to October.

*Plant habit*.—Compact mounding habit.

*Plant height*.—40 cm in overall height, including flower canopy.

*Plant width*.—30 cm to 35 cm in width.

*Plant hardiness*.—Hardy to minus 15° Centigrade.

*Type*.—Perennial.

*Root system*.—Fibrous.

*Propagation*.—Propagation is accomplished using shoot cuttings.

*Cultural requirements*.—Plant in full sun, well-drained and moderately fertile soil and keep well fertilized and watered.

*Time required to produce a rooted cutting*.—5 weeks are needed to produce a rooted cutting.

*Temperature recommended for cuttings to produce roots*.—The air temperature needed is a minimum of 15° Centigrade air temperature and base heat of 21° Centigrade.

*Crop time*.—6 to 9 months is needed to produce a finished 3-liter container size from a well-rooted cutting.

Stem:

*Shape*.—Cylindrical, solid.

*Dimensions*.—15 cm in length, 6 mm diameter.

*Surface*.—Glabrous and glaucous.

*Color*.—145B and 145C.

*Branching*.—Numerous shoots from the axils of the lower leaves.

*Internode length*.—5 mm to 10 mm between nodes (before extension of peduncle).

*Node dimensions*.—5 mm in diameter and 3 mm in length.

Leaf:

*Type*.—Evergreen.

*Dimensions*.—13 to 15 cm in length, 4 mm in width.

*Color* (*adaxial and abaxial surfaces*).—Ranges between 122A and 133B.

*Shape*.—Linear.

*Division*.—Simple.

*Apex*.—Acute.

*Base*.—Decurrent.

*Venation*.—Absent on the adaxial surface and only one central vein visible on the abaxial surface.

*Margins*.—Entire.

*Attachment*.—Sheathing.

*Arrangement*.—Opposite and spiraling up stem.

*Surfaces* (*adaxial and abaxial*).—Glaucous.

*Fragrance*.—Absent.

Flowers:

*Inflorescence*.—Simple cyme.

*Type*.—Double, polypetalous.

*Number*.—5 to 7 per stem.

*Dimensions* (*including calyx*).—45 mm in length and 55 mm in diameter.

*Shape*.—Circular.

*Lastingness*.—10 days at 20° Celsius on the plant; 8 to 10 days off the plant.

*Fragrance*.—Strong, sweet.

*Flowering period*.—May to October.

Peduncle:

*Shape*.—Cylindrical, solid.

*Dimensions*.—20 cm to 30 cm in length, 2 mm to 3 mm in diameter.

*Surface*.—Glabrous, waxy.

*Strength*.—Strong, rigid.

*Color*.—122A.

Bud:

*Shape*.—Obovate.

*Color*.—189B on apical half and 145B on basal half (below the bracts).

*Anthocyanin*.—Absent.

*Dimensions*.—25 mm to 30 mm in length and 8 to 10 mm in width.

Petals:

*Corolla*.—Upper part of corolla convex, lower part of corolla concave.

*Petal arrangement*.—Persistent, apopetalous and overlapping.

*Margin*.—Crenate-dentate.

*Indentations*.—4 mm deep, often narrower.

*Texture*.—Soft.

*Type*.—Double.

*Number of petals*.—25 to 35.

*Dimensions*.—50 mm in length, 31 mm in width.

*Petal shape*.—Fan shape.

*Petal surface*.—Glabrous.

*Petal apex*.—Fan shaped, crenate-dentate.
*Petal base*.—Strap shaped, tapering towards base.
*Color pattern*.—Blade is light magenta when just opening, then white with a magenta band.
*Petal color* (*adaxial surface*).—Ground color of blade when just opened: 75D and 76D. Ground color of blade when mature: Whiter than N155A. Color of band when just opened: N74A to N74B. Color of band when mature: N74B. Color of middle of strap: 145C. Color of base of strap: 145D.
*Petal color* (*abaxial surface*).—Ground color of blade: Whiter than N155A. Color of middle of strap: 145C. Color of base of strap: 145D.

Calyx:
*Dimensions*.—32 mm in length and 12 mm in width.
*Shape*.—Cylindrical.
*Sepals*.—5, fused to 13 mm below the apex.
*Sepal dimensions*.—32 mm in length and 9 mm in width.
*Apex*.—Subacute.
*Base*.—Truncate.
*Color of sepals, outer surface*.—137B fading to 137D at base.
*Color of sepals, inner surface*.—139D.
*Anthocyanin*.—Absent.
*Splitting*.—Not observed.

Epicalyx:
*Number of bracts*.—1 pair of 2.
*Bracts shape*.—Acuminate.
*Bracts dimensions*.—11 mm in length and 8 mm in width.
*Bracts color*.—N138A, N138B, N138C and N138D are all present.
*Anthocyanin*.—Absent.
*Number of bracteoles*.—1 pair of 2.
*Bracteoles shape*.—Acute.
*Bracteoles dimensions*.—12 mm in length and 14 mm in width.
*Bracteoles color*.—N138A, N138B, N138C and N138D are all present.
*Bracteoles anthocyanin*.—Absent.

Reproductive organs:
*Stamen number*.—5 to 10 true stamens. Up to 15 petaloid stamens with misformed anthers have also been observed.
*Stamen dimensions*.—25 to 30 mm length and 0.5 mm diameter.
*Color of filaments*.—Whiter than N155A.
*Anther number*.—5 to 10.
*Anther dimensions*.—3 mm length and 0.5 mm in diameter.
*Color of anthers*.—N74D.
*Anther attachment*.—Dorsifixed.
*Pollen*.—Present, dust color closest to N155A.
*Style number*.—From 2 to 6.
*Style shoulder*.—Absent.
*Color of style*.—Whiter than N155A.
*Style dimensions*.—30 mm to 40 mm in length and 1 mm in width.
*Stigma number*.—One on each style.
*Stigma color*.—White.
*Stigma dimensions*.—Up to 5 mm long along the top of the style, fimbriated zone barely visible, above petals at maturity.
*Ovary position*.—Superior.
*Ovary dimensions*.—10 mm in length and 8 mm in diameter.
*Ovary shape*.—Spindle, often deformed.
*Ovary surface and texture*.—Smooth and slightly ribbed.
*Ovary color*.—145A at the uppermost surface, becoming paler 145C to 145D at the lowest surface.

Seed: Seed has not been observed.

Diseases and pests: Susceptible to known *Dianthus* pests and disease but no other susceptibilities to pests or disease are known.

COMPARISON WITH PARENTAL LINE AND KNOWN VARIETY

'WP15 VAL11' is distinguishable from the male parent as follows. Whereas the plant shape of 'MOW 02.09' is similar to 'WP15 VAL11', the vegetative habit of the two varieties is very different. 'MOW 02.09' is much less vigorous than 'WP15 VAL11' and exhibits shorter flower stems and a tighter habit. In addition, the flower color of 'MOW 02.09' is white with a maroon eye.

'WP15 VAL11' is distinguishable from the female parent as follows. Whereas the flower shape of 'VAL 05.15' is similar to 'WP15 VAL11', the vegetative habit and the flower color of the two varieties are very different. 'VAL 05.15' has wider leaves than 'WP15 VAL11' and 'WP15 VAL11' exhibits many more flower stems and a better overall shape. In addition, the flowers of 'VAL 05.15' are larger and medium pink in color with a darker eye than that of 'WP15 VAL11'.

The variety of *Dianthus* considered to most closely resemble 'WP15 VAL11' is *Dianthus* Plant Named 'Devon Flavia' (U.S. Plant Pat. No. 15,903). In comparison with 'Devon Flavia', 'WP15 VAL11' is approximately one-third taller and bears flowers which are approximately one-third greater in diameter. Whereas the flowers of 'Devon Flavia' are bicolored pink and reddish-purple in color, the flowers of 'WP15 VAL11' are light pink and fuchsia in color.

I claim:

1. A new and distinct cultivar of *Dianthus* plant named 'WP15 VAL11' as described and illustrated herein.

* * * * *